United States Patent
Lee et al.

(10) Patent No.: US 9,774,350 B2
(45) Date of Patent: Sep. 26, 2017

(54) APPARATUS AND METHOD FOR COMPRESSING CONTINUOUS DATA

(71) Applicant: SAMSUNG ELECTRONICS CO., LTD., Suwon-si (KR)

(72) Inventors: So Young Lee, Daejeon (KR); Jin Young Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/341,121

(22) Filed: Nov. 2, 2016

(65) Prior Publication Data
US 2017/0149443 A1    May 25, 2017

(30) Foreign Application Priority Data
Nov. 20, 2015  (KR) .................. 10-2015-0163600

(51) Int. Cl.
| | | |
|---|---|---|
| H03M 7/30 | (2006.01) | |
| H03M 7/46 | (2006.01) | |
| H03M 7/40 | (2006.01) | |
| A61B 5/024 | (2006.01) | |
| A61B 5/145 | (2006.01) | |
| A61B 5/1455 | (2006.01) | |
| A61B 5/00 | (2006.01) | |

(52) U.S. Cl.
CPC ....... *H03M 7/3088* (2013.01); *A61B 5/02416* (2013.01); *A61B 5/1455* (2013.01); *A61B 5/14532* (2013.01); *A61B 5/7232* (2013.01); *H03M 7/3059* (2013.01); *H03M 7/40* (2013.01); *H03M 7/46* (2013.01)

(58) Field of Classification Search
CPC ............. H03M 7/3088; A61B 5/02416; A61B 5/14532; A61B 5/1455; G06T 9/008; H04N 19/94; H04N 19/423; H04N 19/42; H04N 19/86; H04N 19/61
USPC ....................... 341/50–90; 382/253, 300, 232
See application file for complete search history.

(56) References Cited

U.S. PATENT DOCUMENTS

| | | | |
|---|---|---|---|
| 4,464,650 A | 8/1984 | Eastman et al. | |
| 4,558,302 A | 12/1985 | Welch | |
| 4,814,746 A | 3/1989 | Miller et al. | |
| 5,875,213 A * | 2/1999 | Asami ...................... | H04L 1/24 329/300 |

(Continued)

FOREIGN PATENT DOCUMENTS

| | | |
|---|---|---|
| JP | 2001095806 A | 4/2001 |
| JP | 2008310630 A | 12/2008 |

(Continued)

OTHER PUBLICATIONS

Antti Koski: "Lossless ECG encoding", Computer Methods and Programs in Biomedicine, vol. 52, Issue 1, Jan. 1997, pp. 23-33, (11 pages total).

(Continued)

*Primary Examiner* — Lam T Mai
(74) *Attorney, Agent, or Firm* — Sughrue Mion, PLLC (57) ABSTRACT

Disclosed are an apparatus and method for compressing continuous data. The apparatus for compressing continuous data may include a data generator configured to calculate differences between adjacent values in original continuous data and generate data based on the calculated differences.

16 Claims, 7 Drawing Sheets

(56) References Cited

U.S. PATENT DOCUMENTS

| | | | |
|---|---|---|---|
| 6,346,897 B1* | 2/2002 | Roh | H03M 13/05 |
| | | | 341/106 |
| 6,618,615 B1 | 9/2003 | Kimura et al. | |
| 6,798,360 B1* | 9/2004 | Qian | H03M 7/3082 |
| | | | 341/106 |
| 6,810,282 B2 | 10/2004 | Taha et al. | |
| 8,330,596 B2 | 12/2012 | Tanaka et al. | |
| 8,823,560 B1* | 9/2014 | Karkkainen | H03M 7/40 |
| | | | 341/63 |
| 8,976,175 B2* | 3/2015 | Kida | H04N 13/026 |
| | | | 345/419 |
| 2002/0009034 A1* | 1/2002 | Yamaguchi | G11B 7/126 |
| | | | 369/53.26 |
| 2004/0189565 A1* | 9/2004 | Someya | G09G 3/3611 |
| | | | 345/87 |
| 2006/0227018 A1* | 10/2006 | Ejima | G10L 21/038 |
| | | | 341/50 |
| 2008/0118185 A1* | 5/2008 | Jerdev | G06T 3/4015 |
| | | | 382/300 |
| 2009/0252229 A1* | 10/2009 | Cieplinski | H04N 19/139 |
| | | | 375/240.16 |
| 2010/0260256 A1* | 10/2010 | Shigeta | H04N 19/176 |
| | | | 375/240.2 |
| 2015/0018660 A1 | 1/2015 | Thomson et al. | |

FOREIGN PATENT DOCUMENTS

| | | |
|---|---|---|
| JP | 2015088911 A | 5/2015 |
| KR | 1020140067781 A | 6/2014 |
| KR | 1020140104143 A | 8/2014 |

OTHER PUBLICATIONS

Ziv et al: "Compression of Individual Sequences via Variable-Rate Coding", IEEE Transactions on Information Theory, vol. IT-24, No. 5, Sep. 1978, pp. 530-536, (7 pages total).

David A Huffman: "A Method for the Construction of Minimum-Redundancy Codes", Proceedings of the I.R.E., Sep. 1952, pp. 1098-1101, (4 pages total).

* cited by examiner

APPARATUS AND METHOD FOR COMPRESSING CONTINUOUS DATA

CROSS-REFERENCE TO RELATED APPLICATION

This application claims priority from Korean Patent Application No. 10-2015-0163600, filed on Nov. 20, 2015, in the Korean Intellectual Property Office, the disclosure of which is incorporated herein in its entirety by reference.

BACKGROUND

1. Field

Apparatuses and methods consistent with exemplary embodiments relate to data compression technology, and more particularly to an apparatus and method for compressing continuous data.

2. Description of Related Art

Diabetes mellitus is a chronic disease that causes various complications and cannot be easily treated. Thus, the complications should be prevented by regularly checking blood sugar levels. In addition, the blood sugar levels should be checked in order to prepare for low blood sugar and adjust an insulin dose when insulin is injected.

A non-invasive blood sugar measuring method using a near-infrared spectrometer has recently been developed as a blood sugar measuring method. A glucose meter using a near-infrared spectrometer, which is developed to continuously monitor blood sugar levels, predicts blood sugar levels from absorbance data obtained by applying near-infrared rays to skin at a certain time interval.

The absorbance data that is acquired to continuously monitor the blood sugar levels has a vast volume, and thus is necessarily required to be efficiently stored and managed. In particular, the absorbance data is expressed as a value that varies continuously with a change in wavelength, and thus there is a need for a method for efficiently storing and managing such data.

SUMMARY

Exemplary embodiments overcome the above problems and/or disadvantages and other disadvantages not described above. Also, the exemplary embodiments are not required to overcome the disadvantages described above, and may not overcome any of the problems described above One or more exemplary embodiments may provide an apparatus and method for compressing continuous data.

Additional exemplary aspects will be set forth in part in the description which follows and, in part, will be apparent from the description, or may be learned by practice of the presented embodiments.

According to an aspect of an exemplary embodiment, there is provided an apparatus for compressing continuous data, the apparatus including: a data generator configured to calculate differences between adjacent values in original continuous data and generate data based on the calculated differences.

The original continuous data may be one of Photoplethysmograph (PPG) data and absorbance data.

The generated data may include a first value of the original continuous data and the calculated differences.

The apparatus may further include a sign remover configured to compare each of a plurality of values of the generated data with its preceding value to detect a value whose sign is changed, show the sign of the detected value, and remove signs of remaining values The sign remover may show a sign of a first value of the generated data.

The apparatus may further include a decimal point remover configured to remove a decimal point from each of the values of the generated data if the new data comprises values with an identical number of decimal places.

The decimal point remover may remove a zero before a significant digit from each of the values of the generated data.

The apparatus may further include a second compressor configured to compress the generated data from which the signs of the remaining values are removed using a lossless compression algorithm or a lossy compression algorithm.

The lossless compression algorithm may include a run-length encoding (RLE) algorithm, a dictionary-based encoding algorithm, and a Huffman coding algorithm.

According to an aspect of another exemplary embodiment, there is provided a method of compressing continuous data, the method including: calculating differences between adjacent values in original continuous data; and generating data based on the calculated differences.

The original continuous data may be one of PPG data and absorbance data.

The generated data may include a first value of the original continuous data and the calculated differences.

The method may further include comparing each of a plurality of values of the generated data with its preceding value to detect a value whose sign is changed, showing the sign of the detected value, and removing signs of remaining values The method may further include showing a sign of a first value of the generated data.

The method may further include removing a decimal point from each of the values of the generated data if the generated data comprises values with an identical number of decimal places.

The method may further include removing a zero before a significant feature from each of the values of the generated data.

The method may further include compressing the generated data from which the signs of the remaining values are removed using a lossless compression algorithm or a lossy compression algorithm.

The lossless compression algorithm may include an RLE algorithm, a dictionary-based encoding algorithm, and a Huffman coding algorithm.

DETAILED DESCRIPTION

In the following description, like drawing reference numerals are used for like elements, even in different drawings. The relative size and depiction of these elements may be exaggerated for clarity, illustration, and convenience. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Hereinafter, exemplary embodiments will be described in detail with reference to the accompanying drawings. The terms used herein are defined in consideration of the functions of the exemplary embodiments and may be changed depending on a user, the intent of an operator, or a custom. Accordingly, the terms should be defined based on the following overall description of this specification.

Continuous data to be compressed (hereinafter referred to as original continuous data) may be data that is expressed as a value that varies continuously but only slightly. For example, the original continuous data may be biometric data including photoplethysmograph (PPG) data, absorbance data, etc., but is not limited thereto.

Figure 1:
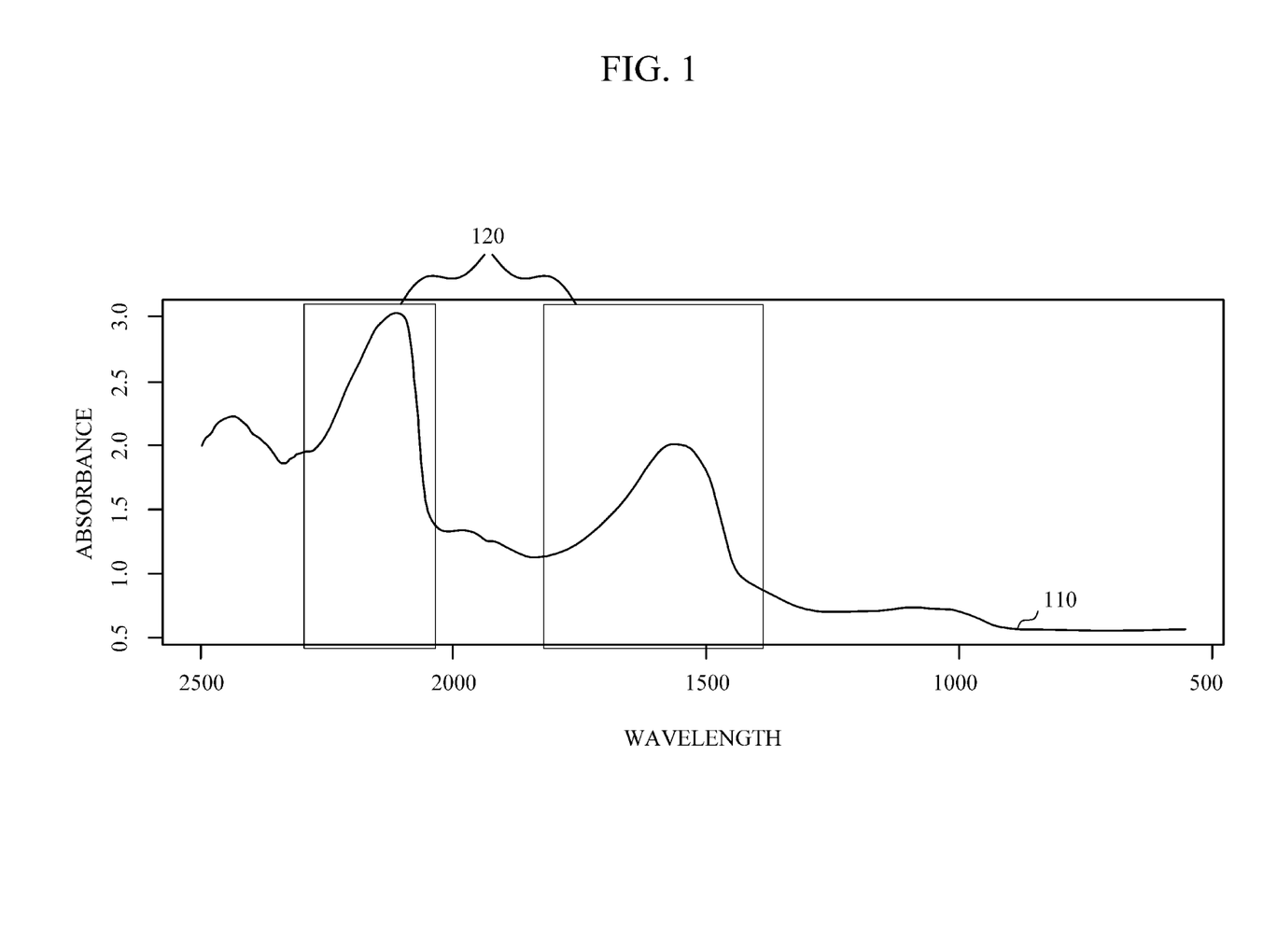
FIG. 1 is a view showing original continuous data according to an exemplary embodiment.

FIG. 1 is a view showing original continuous data according to an exemplary embodiment. The original continuous data of FIG. 1 shows absorbance data 110 measured by applying light to a sample and detecting light scattered or reflected from the sample.

Referring to FIG. 1, the absorbance data 110 may be expressed as one value for each wavelength, and the absorbance data 110 measured from the same sample may have the following characteristics.

First, the absorbance data 110 may be expressed as a value that varies continuously but only slightly. That is, the absorbance data 110 may be changed gradually.

Second, the absorbance data 110 may be similar even when the absorbance data 110 is measured at a different time in regards to the same sample.

Third, the absorbance data 110 may be expressed as values with the same number of decimal places.

Fourth, data at a specific wavelength may be important in analyzing the absorbance data 110. When the concentration of a specific material changes, there is a wavelength at which an absorbance value changes. Accordingly, a value at a corresponding wavelength 120 may be important in analyzing the absorbance data 110.

Figure 2:
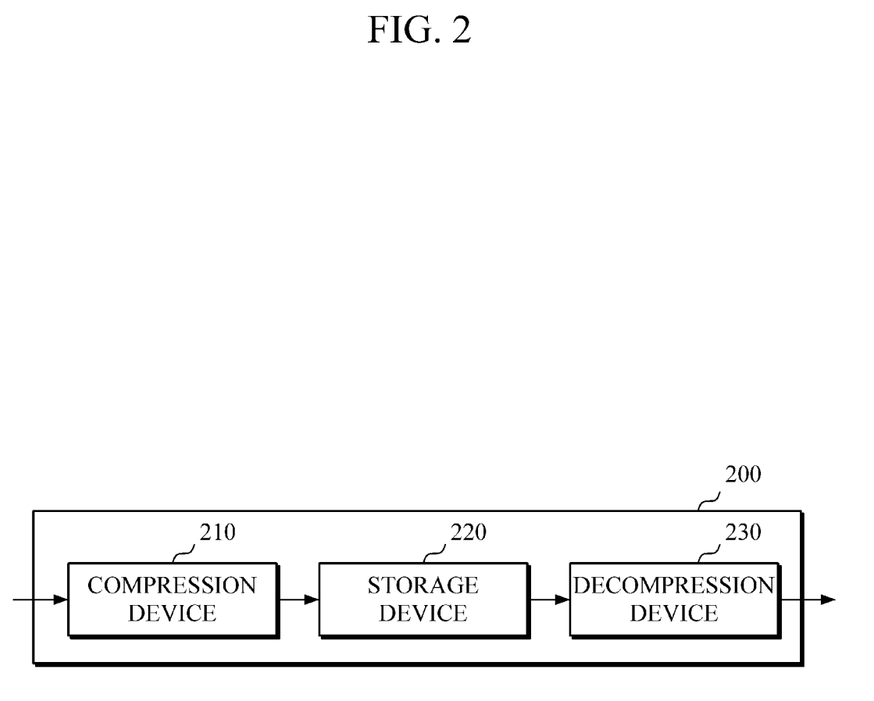
FIG. 2 is a block diagram showing a compression and decompression system according to an exemplary embodiment.

FIG. 2 is a block diagram showing a compression and decompression system according to an exemplary embodiment.

Referring to FIG. 2, a compression and decompression system 200 according to an exemplary embodiment may include a compression device 210, a storage device 220, and a decompression device 230.

The compression device 210 may reduce the amount of original continuous data, and apply various compression algorithms to compress the original continuous data. Here, the compression algorithms may include lossless compression algorithms that may compress data without any loss and lossy compression algorithms that may improve compression rates but lose a portion of the data. The lossless compression algorithms may include a run-length encoding (RLE) algorithm, a dictionary-based encoding algorithm (e.g., a Lempel-Ziv algorithm), a Huffman coding algorithm, etc., and the lossy compression algorithms may include a moving picture experts group (MPEG) algorithm, a joint photographic experts group (JPEG) algorithm, etc., but are not limited thereto.

The compression device 210 will be described later in detail with reference to FIG. 3.

The storage device 220 may store data compressed by the compression device 210. The storage device 220 may include at least one storage medium among a flash memory type memory, a hard disk type memory, a multimedia card micro type memory, a card type memory (e.g., secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc.

The decompression device 230 may apply a decompression algorithm corresponding to the compression algorithm applied to the compression device 210 to restore the original continuous data.

Figure 3:
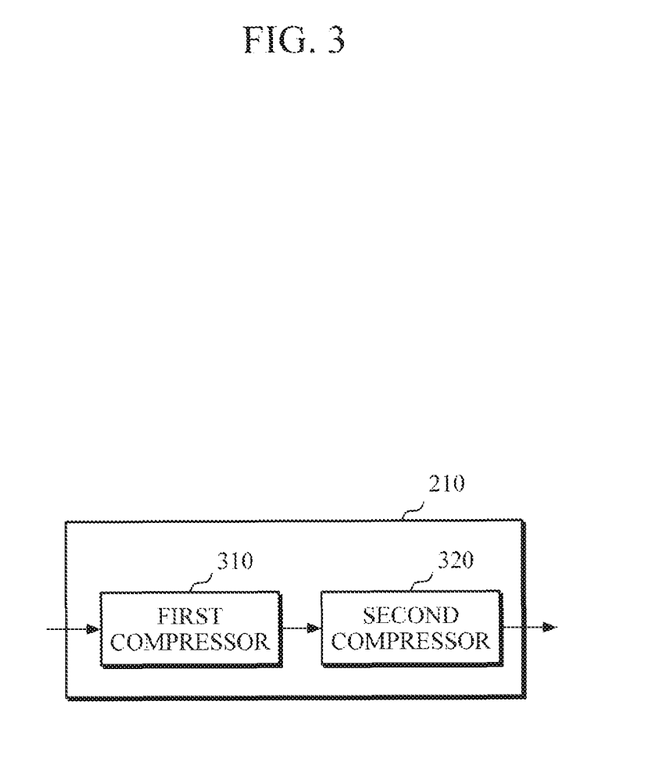
FIG. 3 is a block diagram showing a compression device according to an exemplary embodiment.

FIG. 3 is a block diagram showing the compression device 210 according to an exemplary embodiment.

Referring to FIG. 3, the compression device 210 according to an exemplary embodiment may include a first compressor 310 and a second compressor 320.

The first compressor 310 may reduce the amount of original continuous data to generate new data.

According to an exemplary embodiment, the first compressor 310 may select, from the original continuous data, values of meaningful parts that are important in analyzing the original continuous data and generate new data composed of the selected values.

As described above, for absorbance data used to measure blood sugar levels, absorbance values at a specific wavelength range are important. That is, because the change in concentration of glucose affects absorbance in a specific wavelength range, it is possible to reduce the amount of original continuous data by generating new data composed of the absorbance values at the specific wavelength range.

TABLE 1

| | |
|---|---|
| ORIGINAL CONTINUOUS DATA | 123456 1.12345 1.01234 0.98765 0.87654 0.89012 0.90123 0.91234 0.90012 0.89999 |
| NEW DATA | 1.12345 1.01234 0.98765 0.87654 0.89012 |

Referring to Table 1, for example, the first compressor 310 may select meaningful parts that are important in analyzing the original continuous data, that is, second to sixth values 1.12345, 1.01234, 0.98765, 0.87654, and 0.89012, from the original continuous data, and generate new data composed of the selected second to sixth values 1.12345, 1.01234, 0.98765, 0.87654, and 0.89012.

According to another exemplary embodiment, the first compressor 310 may round off values of the original continuous data to a predetermined number of decimal places and generate new data having a smaller amount than the original continuous data on the basis of a result of the rounding-off.

TABLE 2

| ORIGINAL CONTINUOUS DATA | 1.23456 1.12345 1.01234 0.98765 0.87654 0.89012 0.90123 0.91234 0.90012 0.89999 |
|---|---|
| NEW DATA | 1.235 1.123 1.012 0.988 0.877 0.890 0.901 0.912 0.900 0.900 |

Referring to Table 2, for example, if the values of the original continuous data have five decimal places, the first compressor 310 may round off the values of the original continuous data to three decimal places and generate new data composed of values having three decimal places 1.235, 1.123, 1.012, 0.988, 0.877, 0.890, 0.901, 0.912, 0.900, and 0.900.

According to another exemplary embodiment, the first compressor 310 may select some values of the original continuous data using a multi-variable analysis technique such as Principal Component Analysis (PCA) and generate new data composed of the selected values.

According to another exemplary embodiment, the first compressor 310 may select values from the original continuous data at a predetermined data interval and generate new data composed of the selected values.

As described above, because the absorbance data changes gradually with a change in wavelength, an absorbance value at a specific wavelength is similar to an average of its left and right values. Accordingly, if the original continuous data changes gradually like the absorbance data, it is possible to reduce the amount of data by selecting values from the original continuous data at a certain data interval (e.g., 2) and predicting non-selected values on the basis of the selected values.

In this case, the non-selected values may be predicted using a predefined prediction equation on the basis of values of new data. The prediction equation may be defined as an average of multiple adjacent values and may also be defined as a function for the multiple adjacent values (e.g., a polynomial).

TABLE 3

| ORIGINAL CONTINUOUS DATA | 1.23456 1.12345 1.01234 0.98765 0.87654 0.89012 0.90123 0.91234 0.90012 0.89999 |
|---|---|
| NEW DATA | 1.23456 1.01234 0.87654 0.90123 0.90012 0.89999 |
| PREDICTED | 1.12345 0.94114 0.88885 0.90068 |

Referring to Table 3, for example, if the data interval is 2, the first compressor 310 may select a first value 1.23456, a third value 1.01234, a fifth value 0.87654, a seventh value 0.90123, and a ninth value 0.90012 from the original continuous data and generate new data composed of the selected values. In this case, a tenth value 0.89999 of the original continuous data which is the last value of the original continuous data is difficult to predict upon decompression.

Accordingly, the first compressor 310 may generate new data including the last value, that is, the tenth value 0.89999.

The second value that is not selected from the original continuous data may be predicted as an average 1.12345 of a first value 1.23456 and a second value 1.01234 of the new data. The fourth value that is not selected from the original continuous data may be predicted as an average 0.94444 of the second value 1.01234 and a third value 0.87654 of the new data. The sixth value that is not selected from the original continuous data may be predicted as an average 0.88885 of the third value 0.87654 and a fourth value 0.90123 of the new data. An eighth value that is not selected from the original continuous data may be predicted as an average 0.90068 (rounded off to six decimal places) of the fourth value 0.90123 and a fifth value 0.90012 of the new data.

If the method of reducing the amount of data on the basis of values selected at a predetermined data interval is used, the first compressor 310 may find a difference between a predicted value and an original value and generate prediction difference data on the basis of the difference. The prediction difference data may be used to restore the original continuous data without any loss.

TABLE 4

| ORIGINAL CONTINUOUS DATA | 1.23456 1.12345 1.01234 0.98765 0.87654 0.89012 0.90123 0.91234 0.90012 0.89999 |
|---|---|
| NEW DATA | 1.23456 1.01234 0.87654 0.90123 0.90012 0.89999 |
| PREDICTED | 1.12345 0.94444 0.88885 0.90068 |
| PREDICTION DIFFERENCE DATA | 0 −0.04321 −0.00127 −0.01166 |

Referring to Table 4, for example, if the data interval is 2, the first compressor 310 may select the first value 1.23456, the third value 1.01234, the fifth value 0.87654, the seventh value 0.90123, and the ninth value 0.90012 from the original continuous data and generate new data composed of the selected values and the last value 0.89999.

The first compressor 310 may calculate a difference zero (0) between the non-selected second value 1.12345 and its predicted value 1.12345, calculate a difference −0.04321 between the non-selected fourth value 0.98765 and its predicted value 0.94444, calculate a difference −0.00127 between the non-selected sixth value 0.89012 and its predicted value 0.88885, calculate a difference −0.01166 between the non-selected eighth value 0.91234 and its predicted value 0.90068, and generate prediction difference data composed of the differences 0, −0.04321, −0.00127, and −0.01166.

According to another exemplary embodiment, if the values of the original continuous data have the same number of decimal places, the first compressor 310 may convert the values of the original continuous data into integers and generate new data having a smaller amount than the original continuous data on the basis of a result of the conversion.

As described above, the absorbance data may be expressed as values with the same number of decimal places. Accordingly, if the original continuous data is expressed as values with the same number of decimal places like the absorbance data, it is possible to reduce the amount of original continuous data by deleting a decimal point and a zero before a significant digit from each of the values of the original continuous data to convert the values into integers.

TABLE 5

| ORIGINAL CONTINUOUS DATA | 1.23456 1.12345 1.01234 0.98765 0.87654 0.89012 0.90123 0.91234 0.90012 0.89999 |
|---|---|
| NEW DATA | 123456 112345 101234 98765 87654 89012 90123 91234 90012 89999 |

Referring to Table 5, for example, the first compressor 310 may delete a decimal point and a zero before a significant digit from each of the values 1.23456, 1.12345, 1.01234, 0.98765, 0.87654, 0.89012, 0.90123, 0.91234, 0.90012, and 0.89999 of the original continuous data and generate new data composed of new values 123456, 112345, 101234, 98765, 87654, 89012, 90123, 91234, 90012, and 89999 on the basis of a result of the deletion.

According to another exemplary embodiment, the first compressor 310 may calculate differences between adjacent values of the original continuous data and generate new data having a smaller amount than the original continuous data on the basis of the calculated differences.

As described above, because the absorbance data changes gradually with the change in wavelength, an absorbance value at a specific wavelength has no significant difference from that at its preceding wavelength. Accordingly, if the original continuous data changes gradually like the absorbance data, it is possible to reduce the amount of data by generating new data on the basis of the difference between the adjacent values of the original continuous data.

TABLE 6

| ORIGINAL CONTINUOUS DATA | 123456 112345 101234 98765 87654 89012 90123 91234 90012 89999 |
|---|---|
| NEW DATA | 123456 −11111 −11111 −2469 −11111 1358 1111 1111 −1222 −13 |

Referring to Table 6, for example, the first compressor 310 may calculate differences between adjacent values 123456 and 112345, 112345 and 101234, 101234 and 98765, 98765 and 87654, 87654 and 89012, 89012 and 90123, 90123 and 91234, 91234 and 90012, and 90012 and 89999 of the original continuous data, and generate new data composed of the first value 123456 and the calculated differences −11111, −11111, −2469, −11111, 1358, 1111, 1111, −1222, and −13.

If the method of reducing the amount of data on the basis of the differences between the adjacent values is used, the first compressor 310 may find a difference between the differences to further reduce the amount of data.

TABLE 7

| ORIGINAL CONTINUOUS DATA | 123456 112345 101234 98765 87654 89012 90123 91234 90012 89999 |
|---|---|
| FIRST NEW DATA | 123456 −11111 −11111 −2469 −11111 1358 1111 1111 −1222 −13 |
| SECOND NEW DATA | 123456 −11111 0 8642 −8642 12469 −247 0 −2333 1209 |

Referring to Table 7, for example, the first compressor 310 may calculate differences between adjacent values 123456 and 112345, 112345 and 101234, 101234 and 98765, 98765 and 87654, 87654 and 89012, 89012 and 90123, 90123 and 91234, 91234 and 90012, and 90012 and 89999 of the original continuous data, and generate first new data composed of the first value 123456 and the calculated differences −11111, −11111, −2469, −11111, 1358, 1111, 1111, −1222, and −13.

The first compressor 310 may calculate differences between adjacent values −11111 and −11111, −11111 and −2469, −2469 and −11111, −11111 and 1358, 1358 and 1111, 1111 and 1111, 1111 and −1222, and −1222 and −13 of the generated first new data, and generate second new data composed of the first value 123456 and second value −11111 of the first new data and the calculated differences 0, 8642, −8642, 12469, −247, 0, −2333, and 1209.

According to another exemplary embodiment, the first compressor 310 may reduce the amount of data by generating new data on the basis of the differences between the adjacent values of the original continuous data, comparing each of a plurality of values of the generated new data with its preceding value to detect a value whose sign is changed, showing the sign of the detected value, and removing signs of the remaining values.

As described above, because the absorbance data changes gradually with the change in wavelength, an absorbance value at a specific wavelength has no significant difference from that at its preceding wavelength. Accordingly, if the original continuous data changes gradually like the absorbance data, the differences between the adjacent values have consecutive negative signs (−) or positive signs (+). Accordingly, if there are consecutive negative signs or positive signs, it is possible to further reduce the amount of data by showing only the first sign of the consecutive signs.

TABLE 8

| ORIGINAL CONTINUOUS DATA | 123456 112345 101234 98765 87654 89012 90123 91234 90012 89999 |
|---|---|
| FIRST NEW DATA | 123456 −11111 −11111 −2469 −11111 1358 1111 1111 −1222 −13 |
| SECOND NEW DATA | +123456 −11111 11111 2469 11111 +1358 1111 1111 −1222 13 |

Referring to Table 8, for example, the first compressor 310 may calculate differences between adjacent values 123456 and 112345, 112345 and 101234, 101234 and 98765, 98765 and 87654, 87654 and 89012, 89012 and 90123, 90123 and 91234, 91234 and 90012, and 90012 and 89999 of the original continuous data, and generate first new data composed of the first value 123456 and the calculated differences −11111, −11111, −2469, −11111, 1358, 1111, 1111, −1222, and −13.

The first compressor 310 may generate second new data by comparing each of the values of the first new data with its preceding value to detect a value whose sign is changed (that is, the second value −1111, the sixth value 1358, and the ninth value −1222), showing the signs of the detected values (that is, the second value −1111, the sixth value 1358, and the ninth value −1222), and removing signs of the remaining values.

In this case, as shown in Table 8, by considering that the first value 123456 of the first new data has no preceding value and thus no comparison target, the sign of the first value 123456 of the second new data may also be shown.

According to another exemplary embodiment, the first compressor 310 may calculate differences between reference continuous data that is previously acquired and the original continuous data and generate new data on the basis of the calculated differences.

As described above, the absorbance data has similar values even when the absorbance data is measured at a different time in regards to the same sample. Accordingly, if the original continuous data has similar values even when the original continuous data is measured at a different time like the absorbance data, it is possible to reduce the amount of data by determining the previously acquired continuous data as a criteria and generating new data on the basis of differences with the determined criteria.

TABLE 9

| REFERENCE CONTINUOUS DATA | 123556 113345 101334 99765 88654 90012 90523 91034 89012 79999 |
|---|---|
| ORIGINAL CONTINUOUS DATA | 123456 112345 101234 98765 87654 89012 90123 91234 90012 89999 |
| NEW DATA | −100 −1000 −100 −1000 −1000 −1000 −400 200 1000 10000 |

Referring to Table 9, for example, the first compressor 310 may calculate differences between the reference continuous data and the original continuous data and generate new data composed of the calculated differences −100, −1000, −100, −1000, −1000, −1000, −400, 200, 1000, and 10000.

The above-described various methods for reducing the amount of data may be applied individually or in combination.

The second compressor 320 may apply various lossless compression algorithms or lossy compression algorithms to the generated new data to compress the new data. Here, the lossless compression algorithms may include an RLE algorithm, a dictionary-based encoding algorithm (e.g., a Lempel-Ziv algorithm), a Huffman coding algorithm, etc., and the lossy compression algorithms may include an MPEG algorithm, a JPEG algorithm, etc., but are not limited thereto.

Figure 4:
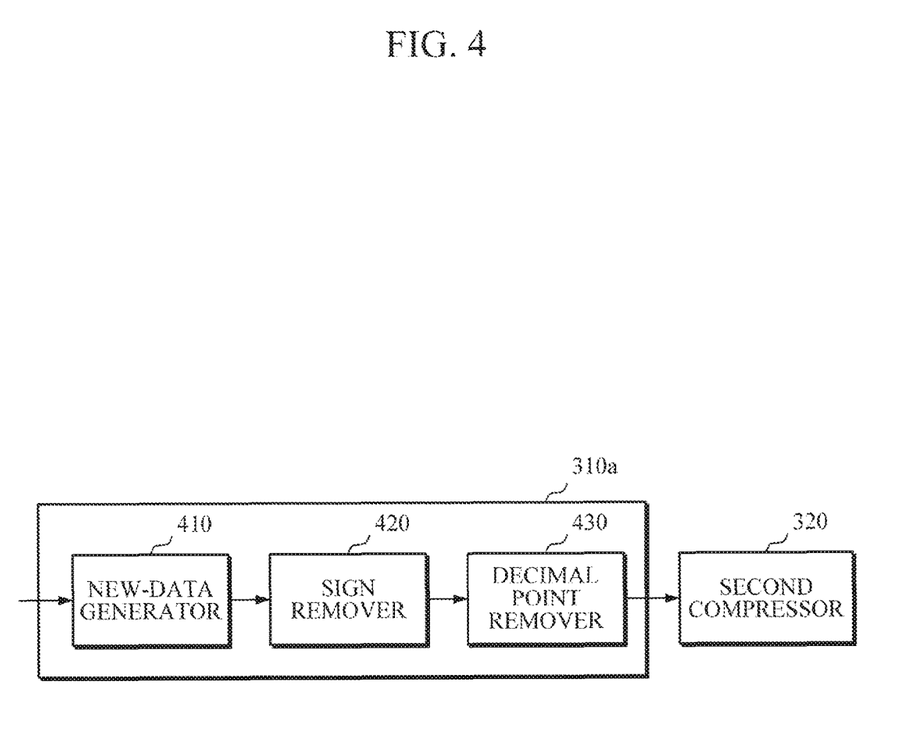
FIG. 4 is a block diagram showing a first compression unit according to an exemplary embodiment.

FIG. 4 is a block diagram showing a first compression unit according to an embodiment. A first compressor 310a is an example of the first compressor 310 of FIG. 1.

Referring to FIG. 4, the first compressor 310a may include a new-data generator 410, a sign remover 420, and a decimal point remover 430.

The new-data generator 410 may calculate differences between adjacent values in the original continuous data and generate new data on the basis of the calculated differences. For example, the new-data generator 410 may calculate the differences between the adjacent values in the original continuous data and generate new data composed of the first value of the original continuous data and the calculated differences.

As described above, because the absorbance data changes gradually with the change in wavelength, an absorbance value at a specific wavelength has no significant difference from that at its preceding wavelength. Accordingly, if the original continuous data changes gradually like the absorbance data, it is possible to reduce the amount of data by generating new data on the basis of the difference between the adjacent values of the original continuous data.

The sign remover 420 may compare each of a plurality of values of the new data generated by the new-data generator 410 with its preceding value to detect a value whose sign is changed, show the sign of the detected value, and remove the signs of the remaining values. In addition, by considering that the first value of the new data has no preceding value and thus no comparison target, the sign of the first value of the new data may also be shown.

As described above, because the absorbance data changes gradually with the change in wavelength, an absorbance value at a specific wavelength has no significant difference from that at its preceding wavelength. Accordingly, if the original continuous data changes gradually, like the absorbance data, the differences between the adjacent values have consecutive negative signs (−) or positive signs (+). Accordingly, if there are consecutive negative signs or positive signs, it is possible to further reduce the amount of data by showing only the first sign of the consecutive signs.

If the values of the generated new data have the same number of decimal places, the decimal point remover 430 may remove a decimal point from each of the values of the new data. In addition, the decimal point remover 430 may remove a zero before a significant digit from the values of the new data.

If the original continuous data is expressed as values with the same number of decimal places, the new data generated on the basis of the differences between the adjacent values of the original continuous data may also be expressed as values with the same number of decimal places as the original continuous data. Accordingly, it is possible to reduce the amount of new data by deleting a decimal point and a zero before a significant digit from each of the values of the new data to convert the values into integers.

Figure 5:
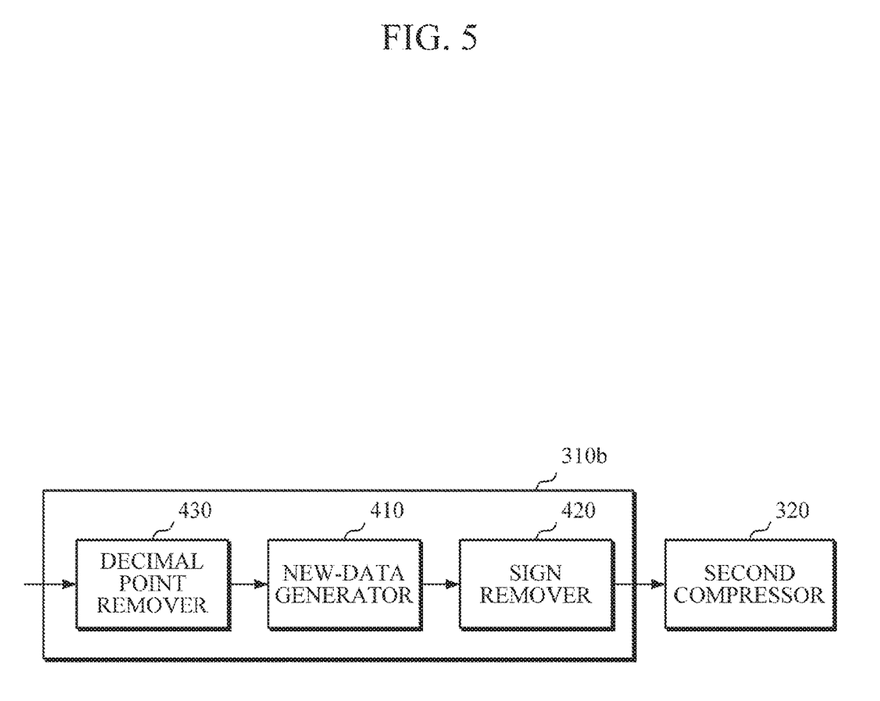
FIG. 5 is a block diagram showing a first compression unit according to another exemplary embodiment.

FIG. 5 is a block diagram showing a first compressor according to another exemplary embodiment. A first compressor 310b is an example of the first compressor 310 of FIG. 3.

Comparing FIG. 4 and FIG. 5, the first compressor 310b of FIG. 5 may be configured to perform a decimal point removal function before a new data generation function.

In other words, the decimal point remover 430 may remove a decimal point and a zero before a significant figure from each of the values of the original continuous data, and the new-data generator 410 may calculate differences between adjacent values in the original continuous data from which the decimal points and the zeros before the significant figures have been removed, and generate new data on the basis of the calculated differences.

Figure 6:
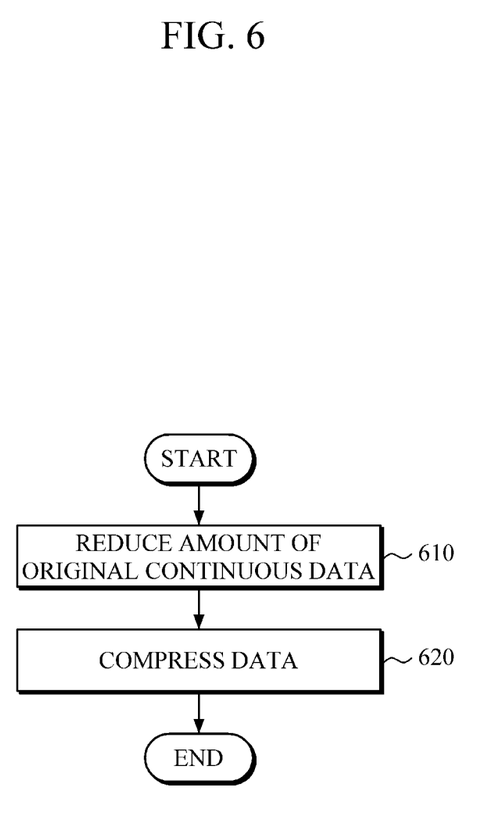
FIG. 6 is a flowchart showing a method of compressing continuous data according to an exemplary embodiment.

FIG. 6 is a flowchart showing a method of compressing continuous data according to an exemplary embodiment.

Referring to FIGS. 3 and 6, the compression device 210 may reduce the amount of original continuous data to generate new data (operation S610).

According to an exemplary embodiment, the compression device 210 may select, from the original continuous data, values of meaningful parts that are important in analyzing the original continuous data and generate new data having a smaller amount than the original continuous data on the basis of the selected values.

According to another exemplary embodiment, the compression device 210 may round off the values of the original continuous data to a predetermined number of decimal places and generate new data having a smaller amount than the original continuous data on the basis of a result of the rounding-off.

According to another exemplary embodiment, the compression device 210 may select some values of the original continuous data using a multi-variable analysis technique such as PCA and generate new data having a smaller amount than the original continuous data on the basis of the selected values.

According to another exemplary embodiment, the compression device 210 may select values from the original continuous data at a predetermined data interval and generate new data having a smaller amount than the original continuous data on the basis of the selected values.

In this case, non-selected values may be predicted using a predefined prediction equation on the basis of values of new data. The prediction equation may be defined as an average of multiple adjacent values and may also be defined as a function for the multiple adjacent values (e.g., a polynomial).

If the method of reducing the amount of data on the basis of values selected at a predetermined data interval is used, the compression device 210 may find a difference between a predicted value and an original value and generate prediction difference data on the basis of the difference. The prediction difference data may be used to restore the original data without any loss.

According to another exemplary embodiment, if the values of the original continuous data have the same number of decimal places, the compression device 210 may convert the values of the original continuous data into integers and generate new data having a smaller amount than the original continuous data on the basis of a result of the conversion. For example, it is possible to reduce the amount of original continuous data by deleting a decimal point and a zero before a significant digit from each of the values of the original continuous data to convert the values into integers.

According to another exemplary embodiment, the compression device 210 may calculate differences between adjacent values of the original continuous data and generate new data having a smaller amount than the original continuous data on the basis of the calculated differences.

According to another exemplary embodiment, the compression device 210 may reduce the amount of data by generating new data on the basis of the differences between the adjacent values of the original continuous data, comparing each of a plurality of values of the generated new data with its preceding value to detect a value whose sign is changed, showing the sign of the detected value, and removing signs of the remaining values.

According to another exemplary embodiment, the compression device 210 may calculate differences between reference continuous data that is previously acquired and the original continuous data, and generate new data on the basis of the calculated differences.

The above-described various methods for reducing the amount of data may be applied individually or in combination.

The compression device 210 may apply various lossless compression algorithms or lossy compression algorithms to the generated new data to compress the new data (operation S620). Here, the lossless compression algorithms may include an RLE algorithm, a dictionary-based encoding algorithm (e.g., a Lempel-Ziv algorithm), a Huffman coding algorithm, etc., and the lossy compression algorithms may include an MPEG algorithm, a JPEG algorithm, etc., but are not limited thereto.

Figure 7:
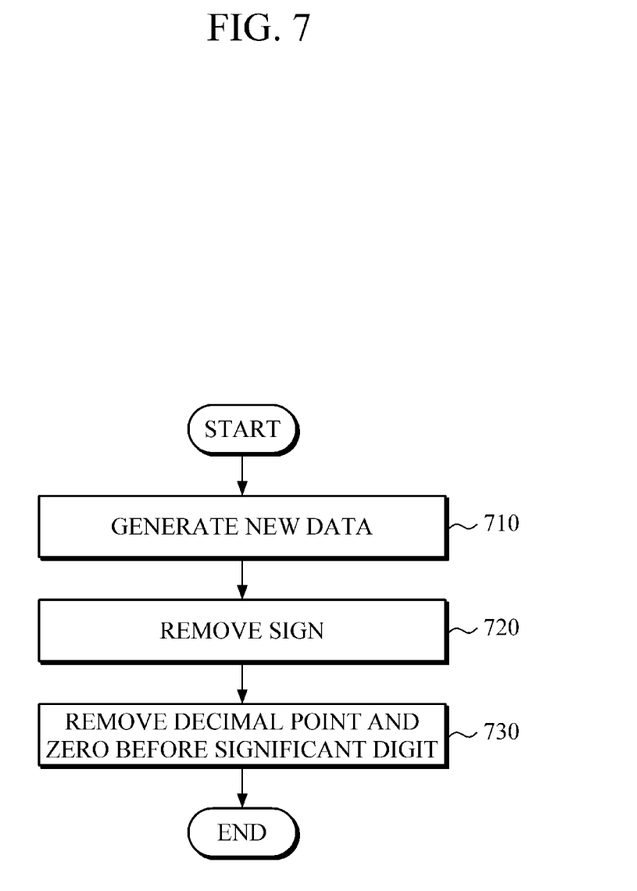
FIG. 7 is a flowchart showing a method of reducing the amount of original continuous data according to an exemplary embodiment.

FIG. 7 is a flowchart showing a method of reducing the amount of original continuous data according to an exemplary embodiment.

Referring to FIGS. 4 and 7, the first compressor 310a may calculate differences between adjacent values in original continuous data and generate new data on the basis of the calculated differences (operation S710). For example, the first compressor 310a may calculate differences between adjacent values in the original continuous data and generate new data composed of a first value of the original continuous data and the calculated differences.

The first compressor 310a may compare each of a plurality of values of the generated new data with its preceding value to detect a value whose sign is changed, show the sign of the detected value in the new data, and remove signs of the remaining values (operation S720). Here, by considering that the first value of the new data has no preceding value and thus no comparison target, the sign of the first value of the new data may also be shown.

If the values of the generated new data have the same number of decimal places, the first compressor 310a may remove a decimal point and a zero before a significant digit from each of the values of the new data (operation S730).

While not restricted thereto, an exemplary embodiment can be embodied as computer-readable codes in a computer-readable recording medium that includes program instructions to be implemented by a computer to cause a processor to execute or perform the program instructions. The medium may also include, alone or in combination with the program instructions, data files, data structures, and the like. The computer-readable recording medium may include any kind of recording devices for storing data which can be thereafter read by a computer system. Examples of the computer-readable recording medium include a ROM, a RAM, a compact disc ROM (CD-ROM), a magnetic tape, a floppy disk, an optical disc, and so on. The described hardware devices may be configured to act as one or more software modules in order to perform the operations and methods described above, or vice versa. In addition, the computer-readable recording medium may be distributed over network-coupled computer systems so that the computer-readable code is stored and executed in a distributed fashion.

Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

While one or more exemplary embodiments have been described with reference to the figures, it should be understood by those skilled in the art that various changes in form and details may be made therein without departing from the spirit and scope as defined by the appended claims. Therefore, the description of the exemplary embodiments should be construed in a descriptive sense only and not to limit the scope of the claims, and many alternatives, modifications, and variations will be apparent to those skilled in the art.

What is claimed is:

1. An apparatus for compressing continuous data, the apparatus comprising:
a first compressor comprising:
a data generator configured to calculate differences between adjacent values in original continuous data and generate data based on the calculated differences; and
a sign remover configured to compare each of a plurality of values of the generated data with its preceding value to detect a value whose sign is changed, show a sign of a detected value, and remove signs of remaining values.

2. The apparatus of claim 1, wherein the original continuous data is Photoplethysmograph (PPG) data or absorbance data.

3. The apparatus of claim 1, wherein the generated data comprises a first value of the original continuous data and the calculated differences.

4. The apparatus of claim 1, wherein the sign remover is configured to show a sign of a first value of the generated data.

5. The apparatus of claim 1, further comprising a decimal point remover configured to remove a decimal point from each values of the generated data if the generated data comprises values with an identical number of decimal places.

6. The apparatus of claim 5, wherein the decimal point remover is configured to remove a zero before a significant digit from the values of the generated data.

7. The apparatus of claim 1, further comprising a second compressor configured to compress the generated data from which the signs of the remaining values are removed using a lossless compression algorithm.

8. The apparatus of claim 7, wherein the lossless compression algorithm is one of a run-length encoding (RLE) algorithm, a dictionary-based encoding algorithm, and a Huffman coding algorithm.

9. A method of compressing continuous data, the method comprising:
    calculating, by a first compressor, differences between adjacent values in original continuous data;
    generating, by the first compressor, data based on the calculated differences; and
    comparing, by the first compressor, each of a plurality of values of the generated data with its preceding value to detect a value whose sign is changed, showing a sign of a detected value, and removing signs of remaining values.

10. The method of claim 9, wherein the original continuous data is Photoplethysmograph (PPG) data or absorbance data.

11. The method of claim 9, wherein the generated data comprises a first value of the original continuous data and the calculated differences.

12. The method of claim 9, further comprising showing, by the first compressor, a sign of a first value of the generated data.

13. The method of claim 9, further comprising removing, by the first compressor, a decimal point from each values of the generated data if the generated data comprises values with an identical number of decimal places.

14. The method of claim 13, further comprising removing, by the first compressor, a zero before a significant digit from each of the values of the generated data.

15. The method of claim 9, further comprising compressing the generated data from which the signs of the remaining values are removed using a lossless compression algorithm.

16. The method of claim 15, wherein the lossless compression algorithm is one of a run-length encoding (RLE) algorithm, a dictionary-based encoding algorithm, and a Huffman coding algorithm.

* * * * *